Figure 1:
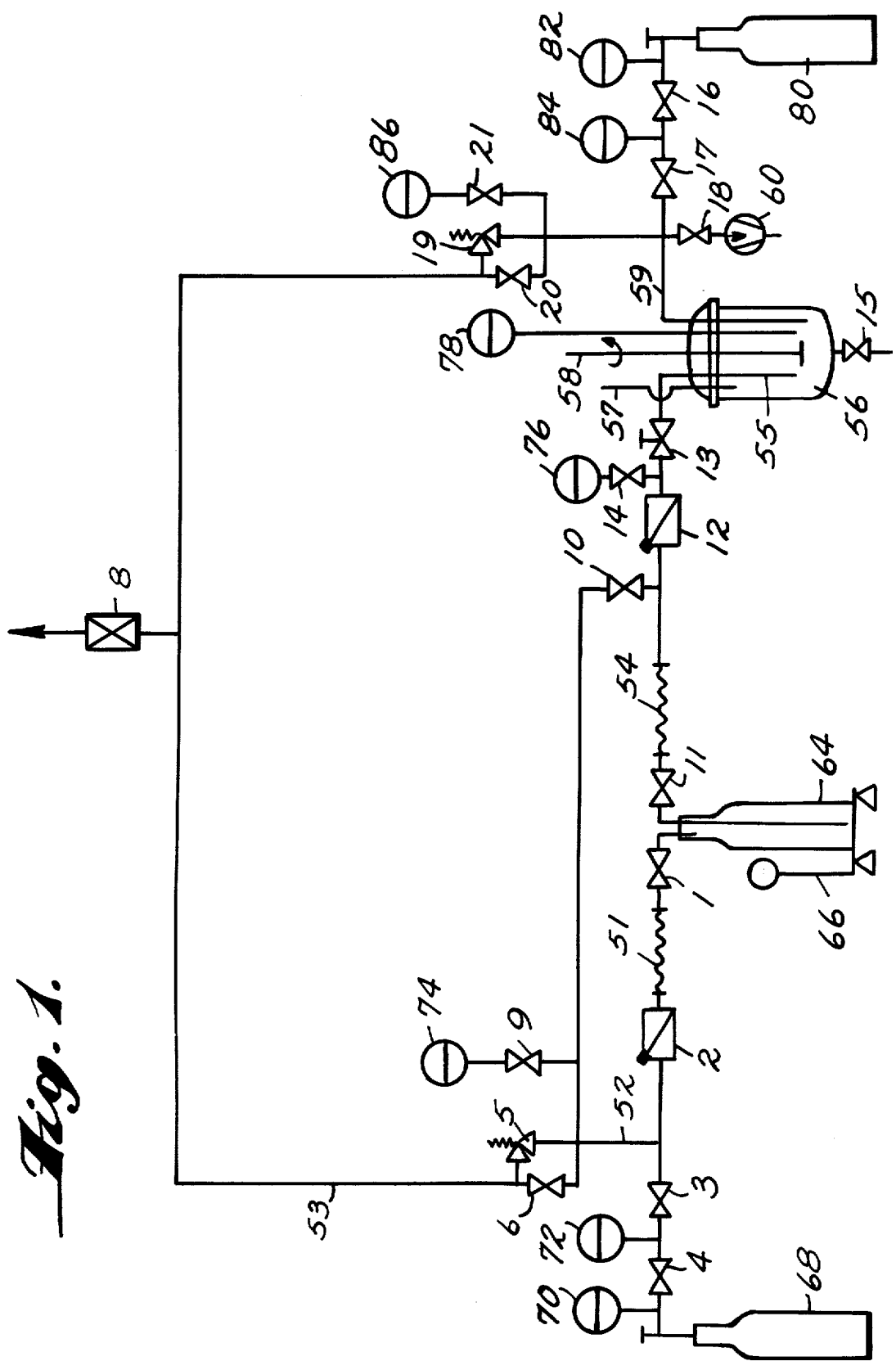

United States Patent [19] [11] 3,933,813
Beschke et al. [45] Jan. 20, 1976

[54] PROCESS FOR THE PRODUCTION OF MERCAPTOETHYL CONTAINING COMPOUNDS

[75] Inventors: Helmut Beschke; Heribert Offermanns, both of Grossauheim; Wilhelm-Alfons Schuler, Bad Homburg, all of Germany

[73] Assignee: Deutsche Gold- und Silber-Scheideanstalt vormals Roessler, Germany

[22] Filed: Dec. 29, 1972

[21] Appl. No.: 319,848

[30] Foreign Application Priority Data
Jan. 14, 1972 Germany............................. 2201633

[52] U.S. Cl. 260/247.1 R; 260/239 BC; 260/243 R; 260/243 B; 260/243 AN; 260/256; 260/268 R; 260/283 S; 260/293.85; 260/309; 260/326.12 R; 260/326.2; 260/326.5 S; 260/326.84; 260/327 E; 260/455 R; 260/481 R; 260/534 S; 260/568; 260/570.6; 260/570.8 R; 260/570.9; 260/583 EE; 260/584 R; 260/609 R
[51] Int. Cl.² ............... C07D 331/02; C07C 149/24; C07C 153/09
[58] Field of Search ...... 260/327 E, 583 EE, 247 R, 260/609 R, 455 R

[56] References Cited
UNITED STATES PATENTS

| 2,185,660 | 1/1940 | Coltof et al. | 260/327 R |
| 3,071,593 | 1/1963 | Warner | 260/327 E |
| 3,317,489 | 5/1967 | Sander | 260/327 E |

FOREIGN PATENTS OR APPLICATIONS

| 465,662 | 5/1937 | United Kingdom | 260/327 E |

OTHER PUBLICATIONS
Braz, J. Gen. Chem. USSR, (1951) pp. 688–693.
Sander, Chem. Rev., Vol. 66, (1966) pp. 298–301 & 328–333.

*Primary Examiner*—Lorraine A. Weinberger
*Assistant Examiner*—Michael Shippen
*Attorney, Agent, or Firm*—Cushman, Darby & Cushman

[57] ABSTRACT

Compounds having a mercaptoethyl group are prepared by reacting an aqueous thiocyanate solution with ethylene oxide in the presence of an inert water immiscible organic solvent to form ethylene sulfide and then reacting the organic phase with a polar organic compound, preferably a secondary amine.

17 Claims, 2 Drawing Figures

PROCESS FOR THE PRODUCTION OF MERCAPTOETHYL CONTAINING COMPOUNDS

The invention is directed to a process for introducing a mercaptoethyl group into organic compounds using ethylene sulfide.

It is known to produce compounds containing a mercaptoethyl group by reacting ethylene sulfide with suitable nucleophilic compounds as, for example, amines, alcohols, mercaptans, acids and suitable acid derivatives at either low or high temperatures with or without solvents, see Houben Weyl "Methoden Der Organischen Chemie," Vol. 9, pages 160 to 166 (1955); Chemical Abstracts Vol. 54 (1960), page 17234c.

The ethylene sulfide employed is produced in a separate process in the following manner: Ethylene oxide is reacted with an aqueous solution of potassium thiocyanate at $-5°$ to $-10°C$. [see, for example, Meade. J. Chem. Soc.(London), pages 1894–1895 (1948)]. To isolate the ethylene sulfide first the potassium cyanate formed must be filtered off with suction, the ethylene sulfide phase separated from the aqueous phase and finally the ethylene sulfide distilled. The tendency of ethylene sulfide to polymerize requires a very careful working under nitrogen in each of these steps since even at 0°C. spontaneous polymerization of the ethylene sulfide takes place very easily. The working up of the ethylene sulfide therefore is very rich in losses even on a laboratory scale.

Besides ethylene oxide forms a solid hydrate at temperatures below $+ 12.5°C$. In all reactions of ethylene oxide in which water participates therefore there should be avoided the reduction of the temperature below this value in the vessels and pipes. This is especially true when working with large amounts of ethylene oxide since in such cases the ethylene oxide for safety reasons should be added in liquid rather than in gaseous form. It is not possible therefore to transfer the known processes for the production of ethylene sulfide on an industrial scale.

Accordingly the production of compounds which contain a mercaptoethyl group from ethylene sulfide on an industrial or large industrial scale is either insufficient or not possible at all.

In contrast according to the invention an aqueous thiocyanate solution is treated with ethylene oxide in the presence of an inert, water immiscible organic solvent and the organic phase reacted with a polar organic compound, which is able to add on to ethylene oxide.

By the process of the invention the disadvantages and difficulties which previously existed in the production and further reaction of ethylene sulfide are removed and this reaction is made possible, for the first time on an industrial and large industrial scale. Furthermore high yields are obtained by the process of the invention. For example, these are considerably higher than in the reaction of the prior art.

The process of the invention is especially suitable for continuous operation.

There are employed in the aqueous thiocyanate solution salts of thiocyanic acid with light metals which are readily water soluble as, for example, alkali metal salts such as sodium thiocyanate, potassium thiocyanate and lithium thiocyanate.

Preferably there is employed potassium thiocyanate.

The aqueous thiocyanate solution preferably contains per mole of thiocyanate 126 cc of water. For example, the amount of water can be between 126 cc and 500 cc per mole of thiocyanate.

According to the process of the invention generally ethylene oxide is added at room temperature although this is not critical. The reaction between ethylene oxide and the thiocyanate is suitably carried out at $+ 5°$ to $+ 50°C.$, preferably at $+ 12.5°$ to $+ 50°C$. Preferably the ethylene oxide is added as a liquid to the reaction vessel. For this purpose it must always be under sufficient pressure that at the particular temperature it is liquid. The lowest pressure, for example at 12.5°C., is 0.2 atmospheres absolute. In general the pressure at which the ethylene oxide is added is between 0.5 to 5.0 atmospheres absolute, but as indicated, this can be varied. Suitably the introduction and reaction of the ethylene oxide takes place in an inert atmosphere, preferably nitrogen. The partial pressure of the nitrogen during the introduction of the ethylene oxide, for example at a temperature of 15°C., is over 0.5 atmospheres absolute, at a temperature of 20°C. over 0.8 atmospheres absolute, at 30°C. over 1.3 atmospheres absolute, at 40°C. over 2.2 atmospheres absolute and at 50°C. over 3.5 atmospheres absolute. As upper boundaries for the partial pressure of nitrogen there can be used, for example 3.3 to 5 atmospheres absolute.

The temperature in the reaction vessel, for example, can be between $+ 12.5°$ and $+ 50°C$. It is convenient during the addition or the introduction of the ethylene oxide to maintain the temperature between $+ 12.5°$ and $+ 30°C.$, especially between $+ 15°$ and $+ 20°C$. Toward the end of the reaction it is generally recommended to increase the temperature, for example to $+ 40°C$. or $+ 50°C$.

The ethylene oxide is added with thorough mixing, for example with stirring. After the end of the addition of the ethylene oxide the mixture is still kept in motion for a while. Generally the additional stirring time is 1 to 8 hours at a reaction temperature between $+ 15°$ and $+ 50°C$. For example, the additional stirring can be for 1 to 6 hours at $+ 15°$ to $+ 30°C$. and subsequently for up to 2 hours at 30° to 50°C. or it can be for 4 hours at 20°C. and then 1 hour at $+ 40°C$.

The organic phase which contains the ethylene sulfide is then separated from the aqueous phase and repeatedly washed with water. To make the phase separation easier it is suitable to add an electrolyte to the water. As electrolyte additives there can be employed, for example, readily water soluble salts of mono or polyvalent cations or anions, especially salts of alkali metal, alkaline earth metals or earth metals with hydrohalic acids, sulfuric acid or phosphoric acid. Examples of such salts are sodium chloride, potassium chloride, calcium chloride, barium chloride, aluminium chloride, aluminium bromide, sodium bromide, potassium bromide, sodium sulfate, potassium sulfate, sodium phosphate, potassium phosphate. Fundamentally there can be used as electrolytes those which are suited for flocculation from an emulsion and known electrolytes, (see, for example Houben-Weyl, "Methoden der organischen Chemie," Vol. I/1 page 218 et seq.). In a given case the electrolyte addition can take place at the first separation of the aquous phase.

The inert organic solvent should not be miscible with water. The solvent should have a specific gravity below 1. For example, there can be employed aromatic and aliphatic hydrocarbons with boiling points up to 250°C., especially between $+ 50°$ and $+ 160°C$.

For example, there can be used aromatic hydrocarbons which can be substituted with one to four lower alkyl groups such as benzene, toluene, xylene (para, meta or ortho isomers or mixtures of them), cumene, ethyl benzene, propyl benzene, mesitylene, 1,2,4-trimethyl benzene, tetramethyl benzenes such as durene, isodurene and prehnitene, cymene, naphthalene, alpha methyl naphthalene, beta-methyl naphthalene and other alkyl substituted naphthalenes, straight or branched chain aliphatic hydrocarbons with six to 15 carbon atoms, e.g. n-hexane, n-heptane, n-octane, n-decane, n-dodecane, n-pentadecane, isooctane, 3,3-dimethylpentane, 2-methylhexane, 3-ethylpentane, 2,3-dimethylbutane, 2,2,3-trimethylbutane, etc.; mono or bicyclic cycloaliphatic hydrocarbons having five and six members in the ring such as cyclopentane, cyclohexane, cis-decalin and derivatives having one to four lower alkyl substituents, especially methyl, ethyl and isopropyl, especially cyclohexane derivatives such as methylcyclohexane, 1,3-dimethyl-cyclohexane, 1-methyl-4-isopropyl-cyclohexane, 1-methyl-3-isopropyl-cyclohexane, propyl cyclohexane or bicyclic hydrocarbons having one aromatic ring such as tetrahydronaphthalene derivatives, for example, Tetralin (tetrahydronaphthalene).

The inert solvent is used, for example, in an amount of 0.5 to 5 kilograms based on 1 kilogram of thiocyanate. The amount of ethylene oxide is about 1.0 to 1.2 moles based on 1 mole of thiocyanate.

In the separation of the ethylene sulfide containing organic phase from the aqueous phase care should be taken that there is the most possible quantitative separation of the aqueous phase or the washing liquid. After the washing the nucleophilic compound to be reacted is immediately added whereupon the reaction occurs, for example, between room temperature and 180°C. The reaction time depends on the particular temperature. The higher the reaction temperature the shorter is the time of reaction. For example, if the reaction is carried out between 60° and 120°C. the reaction time can be between 1 hour and 24 hours. If the temperature is between 80° and 140°C., in a given case it is possible that the reaction can be completed inside 1 to 4 hours.

The organic reactant which is reacted with the ethylene sulfide can be used, for example, in an amount of 0.5 to 1.2 mole based on 1 mole of thiocyanate added. Preferably there is used 0.75 to 1.0 mole of organic reactant per mole of ethylene sulfide. In case it is solid and difficultly soluble in the inert organic solvent the reaction should be carried out in the most finely divided suspension.

Basically there can be employed in the process of the invention any compound which reacts with ethylene sulfide. Especially there can be used compounds which contain primary or secondary amino groups or compounds which contain free hydroxyl or mercapto groups as, for example, aliphatic, aromatic and heterocyclic amines, alcohols, mercaptans and acids as well as the corresponding acid halides and anhydrides. The products prepared according to the invention include, for example, compounds having formula (1) $HSCH_2CH_2-R_3$, or (2) $XCH_2CH_2SCOR_8$ where $R_3$ is

where $R_4$ and $R_5$ are hydrogen, alkyl, aryl or aralkyl and either $R_4$ or $R_5$ can have other substituents attached to the hydrocarbon group. $R_4$ and $R_5$ together with the nitrogen atom can form a heterocyclic ring of five to six atoms which can also contain an additional oxygen, nitrogen or sulfur atom. $R_3$ can also be $OR_6$ where $R_6$ is alkyl or aralkyl or substituted alkyl, $SR_7$ is substituted or unsubstituted alkyl, aryl or aralkyl. X can be halogen, e.g. chlorine or bromine, hydroxyl or $OCOR_8$ where $R_8$ is alkyl, aryl, heterocyclic or substituted alkyl, substituted aryl or substituted heterocyclic.

The reactants which contain an amino group include ammonia and amines of the formulae $R_1NH_2$ and

where $R_1$ and $R_2$ are the same or different alkyl groups of, for example one to 20 carbon atoms, especially one to 10 carbon atoms, which in a given case can be substituted by one more other group. As such groups there may be mentioned cycloalkyl groups, e.g. having three to eight carbon atoms such as cyclopropyl, cyclobutyl, cyclopentyl, cyclohexyl or cyclooctyl, alkoxy groups with one to six carbon atoms, e.g. methoxy, ethoxy and hexoxy, alkylthio groups with one to six carbon atoms, e.g. methymercapto to hexylmercapto, the hydroxy group, the mercapto group, the carboxy group, carbalkoxy groups with one to six carbon atoms, e.g. carbomethoxy and carbohexoxy, halogen, e.g., chlorine or bromine, alkylamino groups with one to six carbon atoms, e.g. methylamino and hexylamino, in a given case substituted by hydroxyl groups, carboxy groups, lower alkyl groups, lower alkoxy groups, carbamide groups, carbalkoxy groups or halogen atoms, e.g. chlorine or bromine, phenyl, phenoxy or phenylamino having one to three substituents or in a given case substituted heterocyclic residues which have one ring or two or three condensed rings with individual rings of five or six members and or more (up to three) heteroatoms such as oxygen, nitrogen or sulfur. Examples of such heterocyclic radicals are radicals which can be derived from indole, imidazole, piperidine, pyrolidene, piperazine, homopiperazine or morpholine, wherein a nitrogen atom can also be substituted by alkyl hydroxyalkyl, benzyl or alkylbenzyl group.

Further examples of a heterocyclic residue are the phenthiazinyl radical and the azaphenthiazinyl radical (for example the 4-aza-phenthiazinylalkyl radical where the alkyl group has two to five carbon atoms). In place of $R_1$ and $R_2$ being alkyl they can be unsaturated, e.g. they can contain a double bond such as the alkenyl group or a triple bond such as alkynyl. The alkyl or unsaturated groups also can be straight or branched chain and can contain one or more of the above mentioned substitutents, e.g. two or three substituents and the substituents can be the same or different. Furthermore as reactants which contain amino groups there can be used cyclic amines of the formula HNA where A is an alkylene radical, especially of three to six carbon atoms which in a given case, can be substituted, especially by alkyl groups of one to six carbon atoms, hydroxy groups, carboxyl groups, phenyl groups or a fused phenyl group (for example tetrahydroquinoline). Besides A can have other hetero atoms such as oxygen, sulfur or, in a given case, a substituted (especially through lower alkyl or hydroxyalkyl) nitrogen atom.

Furthermore, there can be used such as compounds which react with ethylene sulfide alkaloids with primary or secondary amino nitrogen atoms as, for example, piperidine alkaloids (comine), tryptophane alkaloids (abrine) etc.

Individual examples of compounds with amino groups that can be used in the process of the invention are, for example, benzylamine, phenylethylamine, benzedrine, (alpha methyl phenethylamine), pervitine, haloalkylamines such as chloroethylamine, bromoethylamine, bromopropylamine, chloroeicosanyl amine, 3-chloropropylamine, 4-chlorobutylamine and 5-chloroamylamine, allylamine, diallylamine, oleylamine, eicosenylamine, eicosanylamine, octadecylamine, dieicosanylamine, dioctadecylamine, ephedrine, ethylamine, hexylamine, decylamine, methylamine, diethylamine, diisobutylamine, methylethylamine, tridecylamine, vinylamine, tyramine (p-hydroxyphenethylamine), mezcaline, glycine, alanine, valine, leucine, isoleucine, serine, threonine, cysteine, cystine, methionine, tryptophane, tryptamine, histamine, serotonine as well as their alkyl esters, β-amino-alcohols (e.g. ethanolamine, diethanolamine, propanolamine), diphenylalkylamines (having alkyl groups of two to six carbon atoms), xanthinylalkylamines (for example theophylline, theobromine and their derivatives), pyrrolidine, pyrrolidone, piperidine, morpholine, proline, hydroxyproline, indole, imidazole, homopiperazine, thiomorpholine.

As alcohols there can be used, for example, methyl alcohol, ethyl alcohol, isopropyl alcohol, propyl alcohol, butyl alcohol, hexyl alcohol, cyclohexyl alcohol, octyl alcohol, 2-ethylhexanol, 2-octanol, decyl alcohol, isooctyl alcohol, lauryl alcohol, octadecyl alcohol, allyl alcohol, oleyl alcohol, crotyl alcohol, methallyl alcohol, ethylene chlorohydrin propylene chlorohydrin, ethylene bromohydrin, eicosanyl alcohol, benzyl alcohol, phenethyl alcohol, omega chloroeicosanol.

As mercaptans there can be used, for example, methyl mercaptan, benzyl mercaptan, ethyl mercaptan, hexyl mercaptan, amyl mercaptan, lauryl mercaptan, cetyl mercaptan, eicosanyl mercaptan, octadecyl mercaptan, thiophenol, p-tetradecyl thiophenol, thiocresol and mercaptoethanol as well as mercaptides such as sodium methyl mercaptide and potassium ethyl mercaptide.

As acids, acid anhydrides and acid halides, there can be used for example, acetic acid, acetic anhydride acetyl chloride, acetyl bromide, chloroacetyl chloride, chloroacetyl bromide, propionic acid, propionic anhydride, butyric acid, butyryl chloride, butyric anhydride, decanoic acid, decanoyl chloride, stearic acid, oleic acid, palmitoyl chloride, eicosanoic acid, stearoyl chloride.

Naturally it is also possible to add according to the invention known ethylene sulfide stabilizers or antioxidants [see Ullman, "Encyclopaedie der technischen Chemie" (1963), Vol. 14, page 47; Kirk Othmer "Encyclopedia of Chemical Technology," 2nd edition Vol. 2 pages 558–604]. Especially useful as stabilizers are monohydric and dihydric phenols, thiophenols, aminophenols and aminothiophenols such as 2,6-di-t-butyl-p-cresol, butylated hydroxyanisole, 4,4'-thio-bis(6 t-butyl-m-cresol), 4,4'-cyclohexylidene diphenol, 2,5-di-t-amyl hydroquinone, 2,2'-methylene-bis(4-methyl-6-t-butylphenol), p-aminophenol, N-lauryloxy-p-aminophenol, bis [0-(1,1,3,3-tetramethylbutyl) phenol] sulfide, as well as compounds of the group of phenylenediamine, phenylalkyl mercaptans, e.g. phenylethyl mercaptan or phenylalkylsulfides, e.g. dibenzylsulfide. Any of the antioxidants can have lower alkyl substituents. In addition to the compounds just mentioned there can be used thiazines, phenothiazines, aliphatic mercaptans or aliphatic thioethers. Further examples of individual compounds are hydroquinone, pyrocatechol, phenothiazine per se, benzyl mercaptan, butyl mercaptan, dibutyl sulfide, etc. When a satbilizer is added it is recommended that it be used in an amount of 2 to 1,000 ppm (equal to 0.002 to 1%), preferably 10 to 1,000 ppm (0.01 to 1%) or 100 to 1,000 ppm (0.1 to 1%) based on the ethylene sulfide. It is also recommended to add the stabilizer to the organic solvent at the beginning.

The organic sulfur compounds produced by the process of the invention are important intermediates for the chemical industry, especially for the production of medicinal intermediates.

The invention will be understood best in connection with the drawings wherein.

Figure 2:
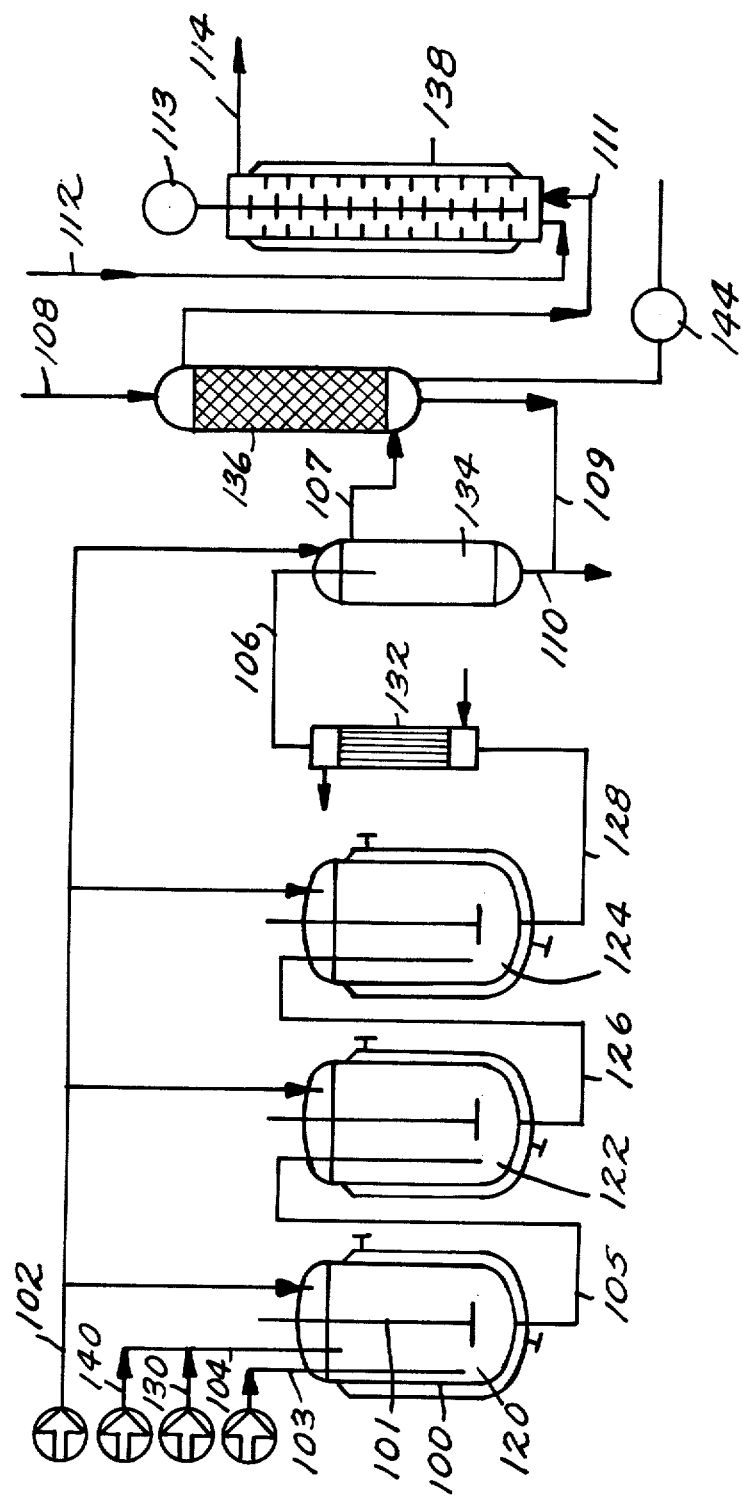

FIG. 1 illustrates in diagrammatic form a preferred process for carrying out the invention and FIG. 2 illustrates a preferred continuous form of carrying out the invention.

While there was employed a 25 liter technical school apparatus in the process described in connection with FIG. 1 it will be appreciated that the process can be carried out with larger (or smaller) apparatus and that there can be used other installations.

Referring more specifically to FIG. 1 of the drawings there is provided an ethylene oxide flask 64 having a double valve (Degesch type) standing on a Tacho balance 66. The flask is connected by way of the green pressure medium valve 1 and a stainless steel metal pipe 51 to the nitrogen flask 68. The connection is by way of the reducing valve 4, the valve 3 and the check valve 2 and contains the manometers 70 and 72. Between valve 3 and the check valve 2 a branch line 52 leads to a safety valve 5 of 10 atmospheres gauge with bypass valve 6 for flushing the waste gas line 53 whose outlet is suitably by way of the dome of a flame trap 8. The branch line 52 also contains the manometer 74 with valves 9 and 10. The ethylene oxide flask 64 is joined to the reaction kettle 56 (for example of 25 liter capacity) by way of gas valve (red) 11, a stainless steel metal pipe 54, a check valve 12, a fine regulating valve 13 and an inlet tube 55. On this line for the liquid ethylene oxide there is also located the side valve 14 for blowing out the line and the manometer 76. The reaction apparatus consists of a coolable (for example with water) and heatable (for example with steam) reaction kettle 56 which besides the inlet tube 55 is provided with a filling opening 57, an outlet valve 15, a stirrer 58, a temperature measuring device with indicator and recorder 78 and the gas inlet of gas line 59. The gas inlet of line 59 is connected to the nitrogen flask 80 by way of reducing valve 16 and valve 17 and is controlled by way of manometers 82 and 84. There is also located in gas line 59 valve 18 to the vacuum sucker with vacuum pump 60, the safety valve 19 with bypass valve 20 as well as manometer 86 with connected valve 21. Valves 21 and 9 serve to close the pressure manometers 86 and 74 in case vacuum is applied.

First all valves in the plant are closed. Then the nitrogen flask 68 is opened (indication of, for example, about 200 atmospheres gauge $N_2$ at 70) and the reducing valve 4 adjusted to 5 atmospheres gauge (indicated at 72). The filled ethylene oxide flask (it should only contain the amount required, in the present case about 2.3 kilograms) is placed on the Tacho balance 66, than a weak nitrogen stream is introduced by way of valves 3 and 10 to flush the metal pipe lines 51 and 54 and the metal pipes were connected to the closed valves 1 and 11 in flowing nitrogen. Strict attention should be paid that the green pressure medium valve 1 is connected to the nitrogen side and the red gas valve is connected to the reactor side. After the connection of the ethylene oxide flask there is built up in the line from flask 68 to valves 1, 11 and 13 a pressure of 5 atmospheres absolute. By closing valve 3 there can be controlled the tightness of the lines to the manometers (74 and 76). Then flushing of line 53 as well as its branches is carried out after opening valve 3 by a brief opening of valve 6 and closing of valve 10. Thereby the preparation of the ethylene oxide side was completed.

Now there is opened the nitrogen flask 80 whereupon the manometer 82, for example indicated about 200 atmospheres absolute pressure and adjusted for example, with valve 16 at 84 to a pressure of 0.5 atmospheres absolute. A vacuum is sucked into the reaction space by way of valve 18, then by way of valve 17 0.5 atmosphere absolute of nitrogen introduced once again vacuum sucked in and nitrogen delivered. Then the waste gas line 53 is flushed with nitrogen by way of valve 20, valves 20 and 17 closed and then after a limited opening of valve 17 with a slight nitrogen stream the reaction vessel is filled through the filling tube, first with aqueous thiocyanate solution and then the inert organic solvent, which in a given case contains a stabilizer.

Subsequently there is delivered by way of valve 17 three times 0.5 atmospheres absolute of nitrogen and again blown by way of valve 20 and then the tightness of the plant tested by adding 0.5 atmospheres absolute of nitrogen and closing all of the valves. To start operation valve 17 is again opened.

Before the start of the plant there are also opened valves 3, 4, 16 and 17.

Valves 6, 1, 11, 10, 13, 20, 18 and 15 are closed.

The manometers indicate for example 200 atmospheres absolute in 70 and 82, 5 atmospheres absolute in 72, 74 and 76, 0.5 atmosphere absolute in 84 and 86.

The stirring is then regulated so that a strong mixing is guaranteed and the inner temperature controlled with cooling so that it is in the range of $+15°$ to $+20°C$. Then there is applied to the ethylene oxide by opening valve 1 the nitrogen pressure of, for example 5 atmospheres absolute, valve 11 opened and carefully valve 13 is opened next so that a similar flow of ethylene oxide takes place to the reaction vessel. As a result at first the pressure at 86 increases but it again is reduced upon good take up.

For an orderly reaction there are the following controls:

1. Weight decrease on the Tacho balance.
2. Pressure fluctuation at 86, for example, between 0.5 and 1.0 atmospheres absolute.
3. Temperature fluctuations at 78 limited by the reaction and periodic cooling.
4. After about 30 minutes the pH value of the solution increases from an initial value of approximately 6.0 to over 12.0; after that the reaction progresses somewhat quicker.

After the corresponding amount of ethylene oxide is taken up, its introduction is ended. Thereby the total space of the line from valve 11 to the reaction vessel must be considered since the entire ethylene oxide is not blown out of the line. Valves 1 and 11 are closed, valve 10 opened and carefully valve 13, whereby the residual ethylene oxide is blown from the line with nitrogen by way of the bypass line. As soon as it is indicated by increase of the manometer 86 that nitrogen by way of valve 13 has filled the apparatus (at the given pressure an increase to over 1 atmosphere absolute) valves 10 and 13 are closed.

Subsequently stirring is carried out for some time, suitably at the same temperature. For this purpose there are closed valves 13, 20, 18 and 15; valves 16 and 17 are opened. The pressure of 86 is, for example, between 0.5 and 1.0 atmospheres absolute.

As soon as the post stirring is ended valves 16 and 17 are closed and valve 20 opened. Thereupon the pressure in the apparatus is raised. Now the temperature is increased (maximum up to $+50°C$.) and stirring continued for some time at the higher temperature. Subsequently flushing is carried out with nitrogen and again cooling to $+20°C$. Under a slight nitrogen stream by way of valves 16, 17 and 20 the lower aqueous phase is drawn off after careful opening of outlet valve 15 and there is added through the filling pipe water or an aqueous salt solution several times, stirred strongly each time for 1 minute and drawn off through valve 15, at the end separation is carried out carefully since no water is permitted in the apparatus. Then there is added with stirring the compound which is to be reacted with the ethylene sulfide (in a given case in an inert organic solvent as, for example, the hydrocarbons mentioned supra) the filling opening closed, flushed several times with nitrogen, the excess pressure reduced and the plant closed at valve 20 and stirred for a long time, whereupon in a given case the temperature is increased. In a given case cooling is carried out subsequently and the pressure reduced by way of valve 20. If the plant is suited for distillation then distillation can be carried out directly from the reaction vessel.

Unless otherwise indicated all parts and percentages are by weight.

EXAMPLE 1

Using the 25 liter apparatus just described after the initial preparations and process conditions as set forth there were put in the reaction vessel first a solution of 3.88 kilograms of potassium thiocyanate (40 moles) in 5.5 liters of water and then 8 liters of toluene which contained 20 grams of butyl mercaptan. Now there were added under strong stirring an equivalent amount of ethylene oxide gas stream. Thereupon the pressure at manometer 86 first increased (higher than 0.5 atmospheres absolute), however, it reduced again after substantial take up to about 0.7 atmospheres absolute. The ethylene oxide was fed at a rate of 1.2 kilograms per hour. After a take up of 1.936 kilograms (44 moles) of ethylene oxide the introduction was completed.

Subsequently stirring was continued for 4 hours at $+20°C$. At the manometer 86 there was a pressure between 0.5 and 1 atmosphere absolute. After the 4 hours the valves 16 and 17 were closed and valve 20 opened. The mixture was heated to $40°C$. and stirring carried out for 1 hour at this temperature. Subsequently flushing was carried out with nitrogen with cooling again to $+20°C$. The lower aqueous phase was drawn off by way of outlet valve 15 under a slight stream of nitrogen and washing was subsequently carried out six times, each time with 8 liters of 5% sodium chloride solution which was added through the inlet pipe whereupon each time strong stirring was carried out for one minute. The aqueous phase was drawn off each time by way of valve 15. After the last washing the mixture was very carefully separated so that no water remained in the apparatus. Then there were added with stirring 2.784 kilograms (32 moles) of morpholine through inlet opening 57 and the latter closed. The reaction vessel was flushed several times with nitrogen, then the excess pressure stopped and the plant closed at valve 20. Now the reaction vessel was carefully heated to + 100°C. within 30 minutes and stirred for 2 hours at this temperature. Thereby there was installed a pressure of about 1.0 atmospheres absolute. Subsequently the pressure was reduced by way of valve 20. The reaction product was distilled whereupon there passed over 4.37 kilograms of morpholinoethyl mercaptan at B.P.$_8$ 93° to 99°C. This corresponds to a yield of 74.4% of theory based on the potassium thiocyanate added and 93.2% of theory based on the morpholine added.

EXAMPLE 2

Operating in the same manner as Example 1 using 2.74 kilograms (32 moles) of piperidine in place of morpholine, there was obtained piperidinoethyl mercaptan B.P.$_8$ 87° to 89°C. in a yield of 88.2% based on the piperidine.

EXAMPLE 3

Operating in the same manner as Example 1 using 4.13 kilograms (32 moles) of dibutyl amine in place of morpholine, there was obtained dibutylaminoethyl mercaptan B.P.$_{26}$ 137° to 140°C. in a yield of 84.4% based on the dibutylamine.

EXAMPLE 4

Operating in the same manner as Example 1 using, however, in place of morpholine a mixture of 3.33 kilograms (32 moles) of amyl mercaptan, 2.18 kilograms (32 moles) of sodium methylate and 10 kilograms of benzene, there were obtained after neutralization with aqueous hydrochloric acid amylmercapto ethyl mercaptan B.P.$_5$ 103° to 107°C. in a yield of 55% (based on the amyl mercaptan) besides 20% of amylmercaptoethylmercaptoethyl mercaptan, B.P.$_5$ 154° to 158°C.

EXAMPLE 5

Operating in the same manner as Example 1 using 3.3 kilograms (32 moles) of the ethyl ester of glycine in place of morpholine, there was obtained N-(β-mercaptoethyl)-glycine ethyl ester B.P.$_2$ 74° to 76°C. in a yield of 61% based on the ethyl ester of glycine.

EXAMPLE 6

Operating in the same manner as Example 1 using 3.62 kilograms (32 moles) of chloroacetyl chloride in place of morpholine, there was obtained 2-chloroethyl thiolochloroacetate B.P.$_3$ 82° to 85°C. in a yield of 62% based on the chloroacetyl chloride.

EXAMPLE 7

This example illustrates the continuous carrying out of the production of B-morpholinoethyl mercaptan as shown in FIG. 2.

The plant for the continuous synthesis consisted of a cascade of three reaction vessels 120, 122 and 124 with cooling jacket 100, stirrer 101, nitrogen inlet 102 and the vessels had outlet tubes 105, 126 and 128. In vessel 120 there is located inlet tube 103 for the ethylene oxide as well as inlet tube 104 for the KSCN solution with branch line 130 through which the toluene is introduced. There is connected to vessel 124 a cooler 132, a separator 134, an extraction column 136 and a plate reactor 138. Reaction vessels 120, 122 and 124 for safety purposes, were held under a nitrogen pressure of 3 atmosphere absolute during the reaction. There were pumped into vessel 120 every hour through line 104 and line 140 a solution of 3.88 kilograms of potassium thiocyanate in 5.5 liters of water as well as 8.0 liters of toluene containing 20 grams of butyl mercaptan and through line 103 1.94 kilograms of ethylene oxide (also every hour). Vessel 120 was filled to such an extent with stirring and cooling to + 20°C. that the average residence time was about 1 hour. The reaction mixture then went through line 105 to vessel 122 and subsequently through line 126 to vessel 124 and then into cooler 132 and from there was pumped through line 106 into the phase separator 134. In vessels 122 and 12 the average residence time was also 1 hour, the temperature was held, for example, in vessel 122 to + 30°C. and in vessel 124 to + 40°C. In the cooler 132 the reaction mixture was cooled to + 15°C. and in phase separator 134 there was a continuous separation of the aqueous phase from the toluene phase. The toluene solution was pumped through line 107 into the extraction column 136 and washed by countercurrent flowing 5% aqueous sodium chloride which was introduced through line 108. Thereupon the contents of extraction column 136 was suitably maintained in motion by a pulsation pump 144 which favors the material exchange in the extraction. The sodium chloride solution flows out through line 109 and can, for example, be combined with the aqueous phase that flows off from separator 134 through line 110. Subsequently the toluene solution is pumped through line 111 into the reactor 138 (for example a plate reactor) having stirrer 113. At this place the toluene solution is mixed with the morpholine that is fed in through line 112 at a rate of 2.78 kilograms per hour. The reactor 138 is, for example, heated with steam at 0.3 atmospheres absolute to 100° to 110°C. The average residence time in reactor 138 is generally 2 hours. The hot reaction mixture is subsequently fed through the line 114 to the distillation unit. The yield corresponded to that of the discontinuous example, i.e., each hour there were produced about 4.35 kilograms of morpholinoethylmercaptan.

What is claimed is:

1. A process for the production of a compound containing a mercaptoethyl group comprising reacting an aqueous alkali metal thiocyanate solution containing 126 cc to 500 cc of water per mole of thiocyanate with ethylene oxide to form ethylene sulfide, said reaction being carried out in the presence of an inert water immiscible organic solvent for ethylene sulfide, said solvent having a specific gravity below 1 and being used in an amount of 0.5 to 5 parts by weight per part by weight of thiocyanate, separating the organic phase containing the ethylene sulfide from the aqueous phase and reacting the ethylene sulfide in the organic phase with an ethylene sulfide reactable polar organic compound selected from the group consisting of primary amines, secondary amines, alcohols, mercaptans, carboxylic acids, carboxylic acid anhydrides and carboxylic acid halides.

2. A process according to claim 1 wherein the treatment of the thiocyanate solution with the ethylene oxide is carried out at a temperature betweeen 12.5° and 50°C.

3. A process according to claim 2 wherein the polar organic compound is a primary or secondary amine.

4. A process according to claim 3 wherein the polar organic compound is a secondary amine of the formula (a) $HNR_1R_2$ or HNA where $R_1$ and $R_2$ are aliphatic groups having one to 20 carbon atoms and A together with the nitrogen atom completes a five to six membered heterocyclic ring having up to one additional hetero atom selected from the group consisting of oxygen, sulfur and nitrogen.

5. A process according to claim 4 wherein $R_1$ and $R_2$ are alkyl groups of one to 10 carbon atoms and HNA is selected from the group consisting of morpholine, piperidine, piperazine, pyrrolidine, proline and hydroxyproline.

6. A process according to claim 1 wherein the polar organic compound is selected from the group consisting of mono alkyl amines having up to 20 carbon atoms, dialkylamines, having up to 20 carbon atoms in each alkyl group, mono alkenyl amines having up to 20 carbon atoms, dialkenyl amines having up to 20 carbon atoms in each alkyl group, monohalo monoalkyl amines having up to 20 carbon atoms, aminoalkanoic acids having up to 20 carbon atoms, aminoalkanoic acids having a phenyl or hydroxyphenyl substituent in the alkanoic acid chain and having up to 20 carbon atoms, mercapto aminoalkanoic acids having up to 20 carbon atoms, hydroxyalkylamines having up to 20 carbon atoms, heterocyclic amino compounds selected from the group consisting of morpholine, thiomorpholine, piperidine, piperazine, pyrrolidine, proline, hydroxyproline, tryptophane, indole, imidazole, pyrrolidone, homopiperazine, tryptamine, serotonine, tyramine, alkanoic acids having up to 20 carbon atoms, anhydrides of alkanoic acids having up to 20 carbon atoms, alkanols having up to 20 carbon atoms, alkenols having up to 20 carbon atoms, aralkenols having up to 20 carbon atoms, alkyl mercaptans having up to 20 carbon atoms, aryl mercaptans having up to 20 carbon atoms and aralkyl mercaptans having up to 20 carbon atoms, haloalkanols having up to 20 carbon atoms, alkanoyl halides having up to 20 carbon atoms.

7. A process according to claim 1 wherein the alkali metal thiocyanate is sodium, potassium or lithium thiocyanate.

8. A process according to claim 1 wherein the solvent is an aromatic hydrocarbon, an aliphatic hydrocarbon or a cycloaliphatic hydrocarbon having five to six carbon atoms in the cycloaliphatic ring.

9. A process according to claim 8 including the step of washing the organic phase with water.

10. A process according to claim 1 including the step of washing the organic phase with water.

11. A process according to claim 1 wherein the polar organic compound is morpholine and the compound produced is β-morpholino-ethyl mercaptan.

12. A process according to claim 11 wherein the treatment of the thiocyanate solution with the ethylene oxide is carried out at a temperature between 12.5° and 50°c.

13. A process according to claim 12 wherein the alkali metal thiocyanate is sodium, potassium or lithium thiocyanate.

14. A process according to claim 13 wherein the solvent is an aromatic hydrocarbon, an aliphatic hydrocarbon or a cycloaliphatic hydrocarbon having five to six carbon atoms in the cycloaliphatic ring.

15. A process according to claim 14 including the step of washing the organic phase with water.

16. A process according to claim 13 wherein the ratio of morpholine to ethylene sulfide is from 0.75 to 1 mole of morpholine per mole of ethylene sulfide.

17. A process according to claim 1 wherein the ratio of polar organic sulfide to ethylene sulfide is from 0.75 to 1 mole of polar organic sulfide per mole of ethylene sulfide.

* * * * *